(12) United States Patent  
Guigné et al.

(10) Patent No.: US 8,277,278 B2  
(45) Date of Patent: Oct. 2, 2012

(54) ACOUSTIC IMAGING WHILE CUTTING

(75) Inventors: Jacques Y. Guigné, Paradise (CA); Nicholas G. Pace, Bath (GB)

(73) Assignee: PanGeo Subsea, Inc., St. John's, NL (CA)

( * ) Notice: Subject to any disclaimer, the term of this patent is extended or adjusted under 35 U.S.C. 154(b) by 689 days.

(21) Appl. No.: 12/488,997

(22) Filed: Jun. 22, 2009

(65) Prior Publication Data

US 2009/0314489 A1 Dec. 24, 2009

Related U.S. Application Data

(60) Provisional application No. 61/075,024, filed on Jun. 24, 2008.

(51) Int. Cl.
*B24B 49/00* (2006.01)
*B24B 51/00* (2006.01)

(52) U.S. Cl. ........... 451/2; 73/627; 166/250.01; 367/86; 451/8; 451/38; 451/51; 451/61

(58) Field of Classification Search ............... 73/152.57, 73/592, 620, 627, 628, 629; 166/250.01; 175/40, 50; 181/123, 105; 451/2, 8, 38, 451/39, 40, 51, 61, 102; 367/25, 27, 35, 367/37, 86
See application file for complete search history.

(56) References Cited

U.S. PATENT DOCUMENTS

| | | | | |
|---|---|---|---|---|
| 5,240,552 | A * | 8/1993 | Yu et al. | 438/5 |
| 5,439,551 | A * | 8/1995 | Meikle et al. | 438/5 |
| 5,496,093 | A * | 3/1996 | Barlow | 299/1.1 |
| 7,073,869 | B2 * | 7/2006 | Nakakuro | 299/81.3 |
| 7,455,568 | B2 * | 11/2008 | Sekiya | 451/2 |
| 7,938,713 | B2 * | 5/2011 | Trieb et al. | 451/2 |

* cited by examiner

*Primary Examiner* — Timothy V Eley
(74) *Attorney, Agent, or Firm* — Richard A. Fagin

(57) ABSTRACT

A method and apparatus for radially cutting tubulars in a downhole environment by emitting acoustic energy into the jet, the acoustic energy having a wavelength selected such that the jet acts as a waveguide, detecting reflected acoustic energy in the jet, and determining the depth of cut from a travel time of the acoustic energy.

8 Claims, 2 Drawing Sheets

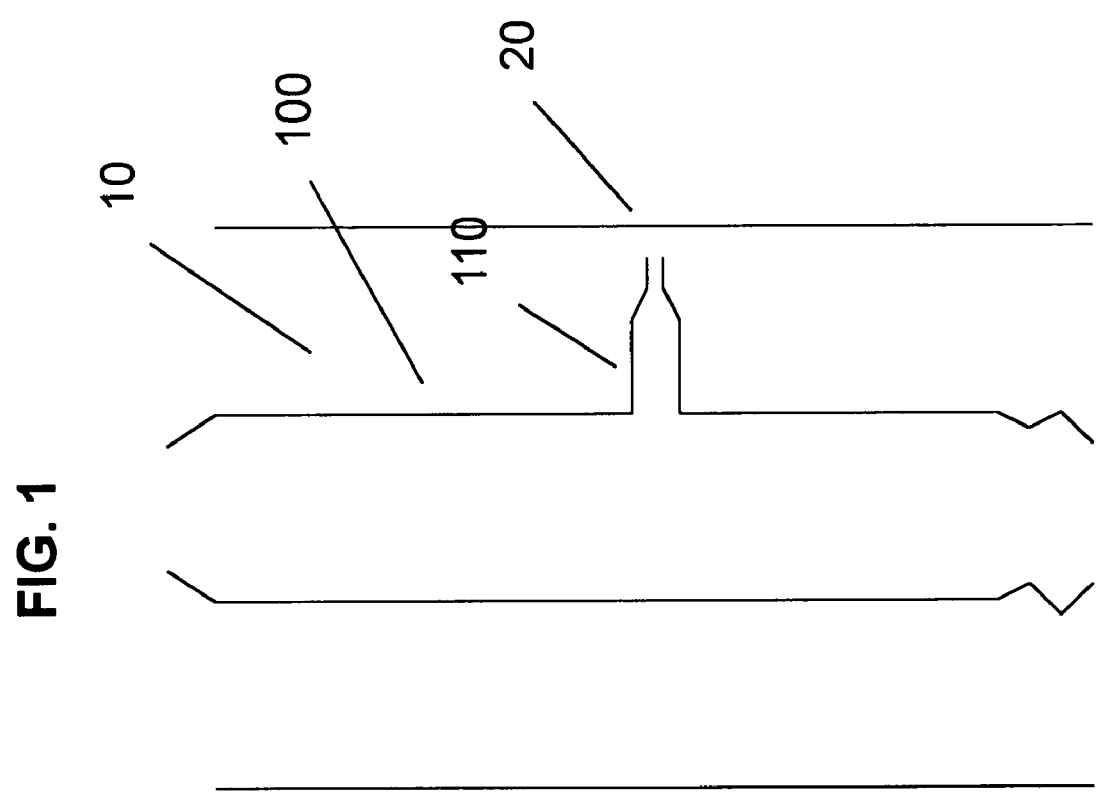

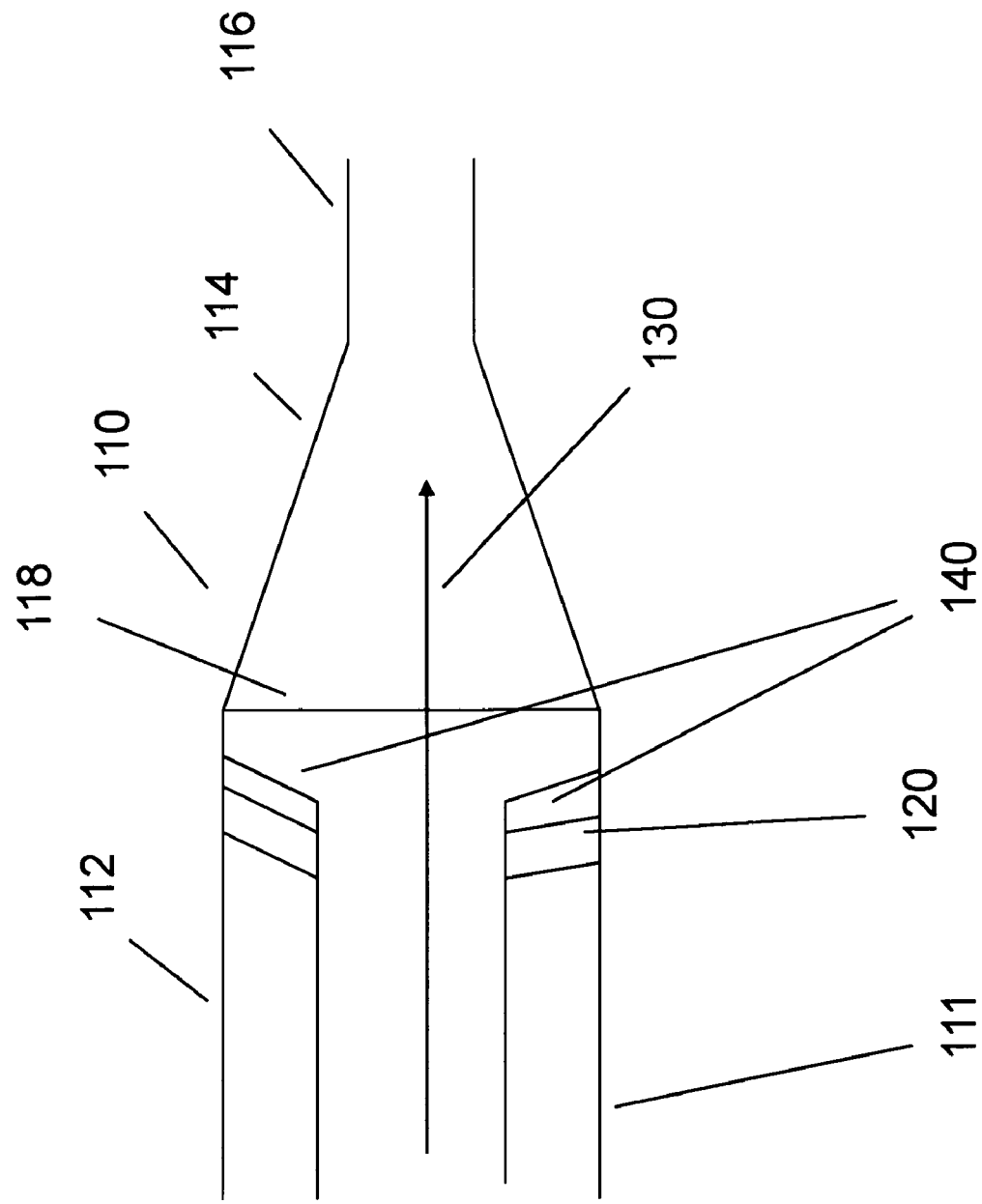

ACOUSTIC IMAGING WHILE CUTTING

CROSS-REFERENCE TO RELATED APPLICATIONS

This patent application claims priority to and the benefit of Provisional Patent Application Ser. No. 61/075,024 filed Jun. 24, 2008, which is hereby incorporated by reference.

STATEMENT REGARDING FEDERALLY SPONSORED RESEARCH OR DEVELOPMENT

Not applicable.

BACKGROUND OF THE INVENTION

1. Field of the Invention

The invention relates generally to the field of downhole pipe cutting tools. More specifically the invention relates to methods and devices for cutting piping downhole using an abrasive water jet.

2. Background Art

Tubular members, for instance, coiled tubing, production tubing, drill pipe, and other items with a hollow space typically may be cut from the inside by inserting a cutting device into the interior hollow space. Hydrocarbon producing wellbores are often lined with tubular members, such as casing, that may be cemented into place within the wellbore. Wellbores may often include additional equipment such as packers and other well completion devices that are secured within a wellbore. Either by design, through wear-and-tear, or by acute damage, these tubular members and other equipment may become unusable and require replacement. Often, a tubular member is secured to the wellbore, and the tubular member must be radially severed at some point along its length in order to remove it from the wellbore. Radially severing a tubular member often requires lowering a downhole cutting tool, such as a tubing cutter, into the well bore for cutting the tubular member.

Various methods have been used to radially sever a tubular member. These methods include rotating cutting heads, electric arcs, cutting torches, and abrasive water jet cutting. In abrasive water jet cutting, a high velocity water jet is discharged through a jet nozzle. The velocity of the water may vary depending on need, but often ranges between 350 and 400 meters/second. The jet typically contains abrasive particles, which together with the high velocity water, cut the tubular member by abrasive action.

It can be difficult to determine when the radial cut about the circumference of the tubular member is complete. This may result in an incomplete cut, possibly requiring additional time spent re-cutting the tubular member. It may also result in an attempt to continue to cut even after the tubular member has been severed. One method used to address this problem has been to include a microphone near the cutting device. An operator may monitor the microphone and listen for a change in sound that may occur when the tubular member has been severed. This method has a number of drawbacks, including the difficulty in distinguishing the completion of the cut from the background noise, particularly in the noisy downhole environment, and variability in operator skill.

SUMMARY OF THE INVENTION

A method for determining depth of cut in a pipe wall of an abrasive fluid jet includes emitting acoustic energy into the jet, where the acoustic energy has a wavelength selected such that the jet acts as a waveguide, detecting reflected acoustic energy in the je. Analysis of changes in the received acoustic signal will indicate when a cut is completed.

In another embodiment of the present invention, a jet for making a radial cut in a tubular member is disclosed. The jet includes a mostly cylindrical jet body having an interior jet wall and a jet throat mechanically connected to the jet body. The jet throat has a jet throat diameter. The jet further includes a jet nozzle that is mechanically connected to the jet body. The jet body, jet throat and jet nozzle are adapted to form a fluid jet by passing fluid through the jet body, jet throat and jet nozzle. The jet further includes an acoustic source disposed on the interior jet wall.

Other aspects and advantages of the invention will be apparent from the following description and the appended claims.

BRIEF DESCRIPTION OF THE DRAWINGS

FIG. 1 shows a schematic depiction of a downhole cutting tool according to one embodiment of the present invention.

FIG. 2 shows a schematic description of a jet according to one embodiment of the present invention.

DETAILED DESCRIPTION

In the present invention, an acoustic source is placed proximate a jet nozzle of a down hole cutting tool. In selected embodiments of the invention, the frequency of acoustic source is 50 kHz or higher.

Referring to FIG. 1, one embodiment of a down hole cutting tool consistent with the present invention is shown. Down hole cutting tool 100 is disposed in wellbore 10 proximate tubular member 20. Jet 110 is in fluid connection with down hole cutting tool 100 such that fluid may flow along the interior of down hole cutting tool and out jet 110 into wellbore 10, forming a fluid jet.

FIG. 2 further depicts jet 110. Jet 110 includes jet body 112, jet throat 114 and jet nozzle 116. The diameter of jet 110 is described by jet throat diameter 118. The fluid is transmitted through jet 110 along fluid flow direction 130. Acoustic source 120 is shown within jet 110.

By placing acoustic source 120 proximate jet nozzle 116, acoustic source 120 may be acoustically coupled to the fluid exiting jet 110, causing jet 110 to act as a waveguide for acoustic source 120. Acoustic source 120 typically includes a transmitter. The transmitter is normally ruggedized for harsh environment usage. As shown in FIG. 2, acoustic source may form a collar around the inside of jet 110. In selected embodiments of the present invention, the transmitter is of a piezo-ceramic type.

In certain embodiments of the present invention, the transmitter is comprised of at least four transducers or elements. These transducers or elements are preferably arranged in such embodiments to produce a resultant angled transmit beam towards the center of jet nozzle 116. The number of transducers or elements used can be increased, or placement around jet 110 ring varied as per the physical dimensions of jet 110 and the signal to noise ratio desired.

With regard to the present invention, for jet 110 to act as a waveguide, its acoustic properties are preferably different from its surroundings. Fluid exiting jet 110 is different from stationary surrounding fluid within wellbore 10 with respect to its velocity, the presence of abrasive particles, and turbulence. Thus, sound energy from acoustic source 120 typically preferentially selects the abrasive fluid jet as a transmitting media due to its movement so as to couple it to the fluid jet via refraction. Once inside the fluid jet, the sound energy from acoustic source 120 is substantially unaffected by the fluid jet velocity and the sound energy from acoustic source 120 moves towards tubular member 20 at approximately the speed of sound in the fluid jet water plus the fluid jet speed. In certain embodiments, the sound wavelength is several times jet throat diameter 118 to allow plane wave propagation to take place, so as to substantially avoid dispersion effects. For instance, where jet throat diameter 118 is less than 1 cm, the frequency of acoustic source 120 is typically between 50 kHz and 150 kHz.

Acoustic source 120, in addition to a transmitter, include hydrophone aor receiving sensors that are acoustically coupled to jet 110 in a similar manner to the transmitter and may be positioned to be consistent with the physical architecture of jet 110. Preferably, the hydrophone and/or receiving sensors are positioned as close to the fluid jet as possible. The hydrophone is preferably calibrated to a frequency response of up to about 200 kHz, but may be calibrated with provision for a higher response if required. One example of a suitable hydrophone is a Brüel & Kjær type 8103 hydrophone with a calibrated frequency response of up to 200 kHz). In select embodiments of the present invention, protective solid horns or waveguides 140 may be used to act as a conduit from the fluid jet to the hydrophone and/or receiving sensors.

In other embodiments of the present invention, acoustic source 120 may include a transducer that acts as both a transmitter and a receiving sensor. Examples include U.S. Pat. No. 5,502,686 issued to Dory et al., or U.S. Pat. No. 5,737,277 issued to Priest, which are incorporated herein by reference. Where transducers are made of ceramic, the transducers may be set into jet wall 111 such that the ceramic is protected by a metal such as a steel or titanium face. In certain embodiments, the transducers are then angled such that on transmission the energy is launched into the jet. One of ordinary skill in the art with the benefit of this disclosure will recognize that various transducer designs appropriate for the downhole environment may be used, including a multilayered design with air or low impedance backing. Such transducers are often shaped like a ring around a tube.

Sensor output from acoustic receiver 120 may be communicated to a recording system. In certain embodiments of the present invention, the recording system may include an analog filter with cut off around 200 kHz. Filter output may be communicated to an analog to digital (A/D) converter and the output may be stored in a computer recording medium such as a hard disc. An A/D converter output may also be sent to a real time analyzer and display. In such embodiments, it is preferable for the digitization rate to be above the Nyquist frequency (400 kHz for 200 Hz acoustic signals), and more preferably at least about 1 Mhz. The recording is preferably adjusted to ensure no data clipping occurs, such as through a trial-and-error methodology. The digitized signals preferably are at least 16 bit dynamic range. The data could be collected and stored in files corresponding to, typically, 1 msec time windows, thus allowing the analysis to provide spectra with 1 kHz resolution. Therefore, if a complete cut of tubular member 20 requires 30 minutes, the storage required would be, at a rate of about 2 Mbytes per sec, approximately 3600 Mbytes or less than about 4 Gbytes.

When cutting tubular members in accordance with the present invention, fluid is displaced into downhole cutting tool 100, through jet 110 and into wellbore 10. Jet 110 is designed to force fluid that exits jet 110 through jet nozzle 116 to form a fluid jet and impinge on tubular member 20. The fluid jet combined with the abrasive particles that exits jet nozzle 116 is adapted to cut tubular member 20.

If the fluid jet does not completely cut through tubular member 20, sound generated by acoustic source 120 is reflected. The reflected acoustic signal can be captured using the hydrophone and/or receiving sensors that are a part of acoustic source 120. The time of arrival history can be monitored to establish the depth of penetration of the cut with respect to time.

When the fluid jet completes its cut through the tubular member, an acoustic change is detected in the reflected signals received by the hydrophones and/or receiving sensors of acoustic source 120. The acoustic change can be tracked as the fluid jet advances along the circumference of tubular member 20 and through multiple casing walls when the tubular member consists of nested casings or pipes. In certain cases, e.g., cutting through the casing wall fully or through all casing walls in nested casings, the signal received by the hydrophones and/or receiving sensors may substantially disappear. Typically, this occurs when only water is present outside the casing or sediment may be present which would produce a unique impedance change but provide substantially no further reflecting boundary.

The hydrophones and/or receiving sensors may receive various returning signals and noise intensities, as well as changes in travel time, forming a unique amplitude/time history which may be analyzed using various transforms known to those of skill in the art, such as the Hilbert Transform, to aid in the discrimination of received signals that indicate the fluid jet has completely cut through tubular member 20 and when it has not. In addition, the reflected signal received by the hydrophones and/or receiving sensors (which may be described as a "noise spectrum") may change when the fluid jet cuts through each casing boundary or layer of tubular member 20 until the fluid jet cuts completely through tubular member 20. This change will often be accompanied by a step change in travel time of the returning signal. Such analysis may characterize these noise spectrum changes and, through visualization software, implement a real-time depth profile of the groove in tubular member 20 being cut by the fluid jet. In this embodiment, the hydrophone and/or receiving sensors of acoustic source 120 monitor and update the analysis and may visually plot the overall discriminatory characteristics of the returning signals, thus providing feedback where extra cutting is needed.

In certain embodiments of the present invention, the transmitter of acoustic source 120 is pulsed, i.e., the sound emitted by the transmitter is intermittent. Pulsing of acoustic source 120 creates time windows in which the background noise may be compared to that of the reflected signal in the appropriate frequency range when a reflected signal is expected, allowing the real time analyzer and display to better distinguish between noise and the reflected signal. In addition to the pulsing of a single frequency transmission, a finite duration frequency sweep (chirp) may be transmitted. These two types of transmission may be sequentially alternate. On reception, compression processing of the chirp signal will give an arrival time that indicates the depth of the cut. As the distances involved are small, high repetition rates are possible and provide the opportunity for signal stacking to enhance the signal to noise ratio. As the jet rotates, so the indications of cutting can be displayed versus the 360 degrees.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining depth of cut in a pipe wall of an abrasive fluid jet, comprising:
    emitting acoustic energy into the jet, the acoustic energy having a wavelength selected such that the jet acts as a waveguide;
    detecting reflected acoustic energy in the jet; and
    analyzing the detected acoustic energy to determine when the cut is completed.

2. The method of claim 1 further comprising determining when the pipe wall is fully severed when one of the following occurs: (i) the detected energy indicates a step change in reflected acoustic energy travel time or (ii) there is a substantial absence of detected reflected acoustic energy.

3. The method claim 1, wherein the step of determining the depth of cut from a travel time of acoustic energy further comprises forming an amplitude/travel time history of detected reflected acoustic energy.

4. The method of claim 3, wherein the step of determining the depth of cut from a travel time of acoustic energy further comprises analyzing the amplitude/travel time history using a Hilbert Transform.

5. A method for severing a pipe wall of a first tubular section comprising:
    discharging an abrasive fluid jet from a jet nozzle such that the abrasive fluid jet cuts into the first tubular section;
    emitting acoustic energy into the abrasive fluid jet, the acoustic energy having a wavelength selected such that the abrasive fluid jet acts as a waveguide;
    detecting reflected acoustic energy in the abrasive fluid jet; and
    analyzing the detected reflected acoustic energy to determine when a cut in the pipe wall is completed.

6. The method of claim 5 further comprising using the abrasive fluid jet to sever a second tubular section wherein the first tubular section is nested inside the second tubular section.

7. The method of claim 5, wherein the step of emitting acoustic energy into the abrasive fluid jet is pulsed such that the acoustic energy emitted is intermittent.

8. The method of claim 7 further comprising comparing the reflected acoustic energy in the abrasive fluid jet to a background acoustic energy.

* * * * *